United States Patent [19]

Seto et al.

[11] Patent Number: 5,077,202

[45] Date of Patent: Dec. 31, 1991

[54] PROCESS FOR PRODUCING A GLYCOLIPID HAVING A HIGH EICOSAPENTAENOIC ACID CONTENT

[75] Inventors: Akira Seto, Kanagawa; Kiyohiro Kitagawa, Chiba; Shoko Yamashita; Tadasu Fujita, both of Kanagawa, all of Japan

[73] Assignee: Nisshin Oil Mills, Ltd., Tokyo, Japan

[21] Appl. No.: 770,509

[22] Filed: Aug. 28, 1985

[30] Foreign Application Priority Data

Sep. 5, 1984 [JP] Japan .................................. 59-184550

[51] Int. Cl.$^5$ .......................... C12P 7/64; C12P 7/62; C12P 19/02; C12N 1/12
[52] U.S. Cl. .................................... 435/134; 435/105; 435/257; 435/135; 260/412; 260/420
[58] Field of Search ............... 435/105, 134, 946, 257; 260/412, 412.4, 420, 428.5

[56] References Cited

U.S. PATENT DOCUMENTS 4,615,839  10/1986  Seto et al. ......................... 260/420

OTHER PUBLICATIONS

Kirk-Othmer, *Encyclopedia of Chemical Technology*, Second Ed., vol. 1, p. 460 (1963).

*Primary Examiner*—Douglas W. Robinson
*Assistant Examiner*—Irene Marx
*Attorney, Agent, or Firm*—Kane, Dalsimer, Sullivan, Kurucz, Levy, Eisele & Richard

[57] ABSTRACT

A process for producing a glycolipid having a high eicosapentaenoic acid (EPA) content is provided, which process comprises fractionating the whole lipids of marine chlorella by means of a combination of solvent-fractionation with column chromatography, which glycolipid has platelet agglutination-inhibiting effect, serum cholesterol-increase-inhibiting effect, etc. of EPA and also having a higher absorption rate in intestinal canal than EPA triglyceride or ethyl ester.

5 Claims, No Drawings

PROCESS FOR PRODUCING A GLYCOLIPID HAVING A HIGH EICOSAPENTAENOIC ACID CONTENT

BACKGROUND OF THE INVENTION

1. Field of the Invention

This invention relates to a process for producing a glycolipid having a high content of eicosapentaenoic acid (hereinafter referred to as "EPA") from marine Chlorella

2. Related Art Statement

EPA is a substance which, in recent years, has been confirmed to be effective as a medicine for prophylaxis and therapy of brain thrombus and vascular sclerosis. This EPA has been known to be contained in fish oils and marine plants (algae) oils, and a triglyceride having an EPA purity of about 20 to 30% has been subjected to fractional purification from fish oils and commercially available as a product for healthy foods. On the other hand, an EPA ethyl ester having a EPA purity of 80% or higher as a product for pharmaceuticals has also been prepared as trial. However, fish oils have a high content of highly unsaturated fatty acids having similar properties to those of EPA such as docosahexaenoic acid; hence when fish oils are used as raw material, EPA content is at most about 20%. Thus in order to raise EPA ethyl ester content up to 80% or more, it is necessary to effect it by combining some of various processes such as urea adduct process, solvent-fractionation process, fractional distillation process, column chromatography, etc., but this is not easy due to complicated operations. Further, it cannot be said that the absorption efficiency of a high purity EPA ethyl ester within intestinal canal is so good; hence in this respect, too, a product having a high absorption efficiency has been desired.

SUMMARY OF THE INVENTION

The object of the present invention is to provide a process for producing a substance having a high EPA content and superior absorption properties, with good efficiency and with simplification.

The present invention resides in a process for producing a glycolipid having a high EPA content which comprises fractionating the whole lipids of marine Chlorella by way of extracting the whole lipids of marine Chlorella with a mixed solvent of a polar solvent with a non-polar solvent, thereafter removing the solvent from the extracted fluid, then washing the residue with a non-polar solvent, and then subjecting the insoluble substance to column chromatography.

The lipids of marine Chlorella are fractionated by way of solvent fractionation and column chromatography into phospholipid, glycolipid, triglyceride and others. The total content of lipids in marine Chlorella on the dry weight basis is as high as 35% to 40%, and about 20 to 30% thereof corresponds to glycolipid aimed in the present invention.

DETAILED DESCRIPTION OF PREFERRED EMBODIMENTS

The present inventors have made extensive research in order to find a production process by which a substance suitable to the above-mentioned object can be obtained, and as a result have found the following facts: In order to achieve the above object, it has been first considered that the starting raw material should be obtained rather from fish oils than from marine algae. It has already been reported in a number of literatures that the lipids of marine algae contain a relatively high concentration of EPA, but in the case of algae, the lipids have an extremely low content thereof of 5% or less on the dry weight basis.

Thus we investigated the lipids of marine Chlorella to obtain the following interesting results:

(1) The total lipid content in marine Chlorella is as high as 35% to 40%;

(2) as to the fatty acid composition of the whole lipids, EPA therein is also as high as 40%; and (3) when the whole lipids are fractionated by way of solvent-fractionation and silica gel chromatography into phospholipid, glycolipid, triglyceride and others, it has been found that the proportion of EPA in the whole fatty acids contained in the glycolipid is as very high as 70% or more.

It has been known that in general, among all the lipids contained in marine algae, particularly glycolipid has a high content of EPA. However, in the case of marine Chlorella, the total lipid content on the dry weight basis is as high as 35 to 40%, and further about 20 to 30% thereof (hence 8 to 12% on the dry weight basis) is glycolipid; thus it is considered that marine Chlorella is most preferable as a glycolipid-feeding source aimed in the present invention.

The glycolipid is characterized in that it has physiological effects of EPA such as platelet agglutination-inhibiting effect, serum cholesterol increase-inhibiting effect, etc., and yet it has also a higher absorption rate in intestinal canal than triglyceride or ethyl ester of EPA.

The marine Chlorella usable in the present invention is not limited to particular genuses and species so long as it has a high content of EPA, but usually marine Chlorella classified under Chlorella minutissima, etc. are used.

First, powder of such a marine Chlorella is subjected to the extraction of lipids with a mixture of polar and non-polar organic solvents in an optional proportion, followed by removing the solvents, thereafter removing neutral lipid, chlorophyl and sterols. With a non-polar solvent such as ether, washing the resulting fraction with acetone and collecting substances which disslve out to obtain raw fractions of glycolipid. However, only by way of such a method, there occurs a large quantity of loss or other components mixed in; thus when all the resulting fractions are re-fractionated by means of silica column chromatography to collect glycolipid fraction, a high purity glycolipid is obtained with a high yield. However, such a fractional method shown herein is an example of the methods, and the fractional method of glycolipid according to the present invention should not be construed to be limited thereto.

The present invention will be described in more detail by way of Examples.

EXAMPLE 1

From dry powder of a marine chlorella (chlorella minutissima) (1 kg) were extracted the whole lipids with a mixed solvent of chloroform and methanol (2:1) to obtain extracted lipids (380 g), followed by removing the solvents, adding diethyl ester (2 l) to the resulting whole lipids, sufficiently mixing these materials, removing neutral lipid, sterols and chlorophyl, recovering ether-insolubles through filtering, dissolving the resulting material in a small quantity of a mixed solvent of chloroform and methanol (2:1), subjecting the solution to silica gel column chromatography, to successively develop it with chloroform-methanol (2:1), chloroform-methanol (1:1) and methanol in this order, checking the resulting respective fractions by means of thin-layer chromatography to find the peak of aimed glycolipid component, collecting the fractions and removing the solvents to obtain a glycolipid component (about 90 g). The fatty acid composition thereof is shown in Table 1.

TABLE 1

| Fatty acid | 16:0 | 16:1 | 18:0 | 18:1 | 18:2 | 18:3 | 20:4 | 20:5 |
|---|---|---|---|---|---|---|---|---|
| % | 4.2 | 4.2 | — | — | 1.1 | — | 7.0 | 76.0 |

In the above Table, the proportions (16:0, - - -, 20:5) in the column of fatty acid mean carbon number of fatty acid: number of unsaturated bonds.

The thus obtained glycolipid was confirmed to have a high content of EPA (carbon number of fatty acid: number of unsaturated bonds=20:5) of 76.0%, as shown in Table 1. Further, in order to confirm the structure of the sugar part of this glycolipid, this glycolipid was subjected to acid hydrolysis, followed by collecting the sugar part and then subjecting it to enzymatic analysis according to conventional method.

As a result, this sugar was estimated to be galactose since it reacted specifically with galactosehydrogenase. Further the galactose content was estimated to be about one mol per mol of the glycolipid. Thus the glycolipid is confirmed to be monogalactosyl diglyceride the sugar component of which is composed mainly of galactose.

EXAMPLE 2

With a glycolipid component obtained in the same manner as in Example 1 (hereinafter referred to as GL) and EPA ethyl ester (hereinafter referred to as EPA-EE) (purity: 70%), their platelet agglutination-inhibiting effects were subjected to comparison study. Namely, GL and EPA-EE, both adjusted so as to give the same EPA dose taking their EPA contents into account, were administered to rats (body weight: 150 g) in a dose of 0.5 g/day as EPA according to forced administration method by way of stomach tube, over 10 days. In addition, feeding stuff was given under free intake. After completion of the administration, the rats were subjected to one night starvation and then to blood letting. Platelet rich plasma and platelet poor plasma were collected in a convention manner according to centrifugal separation method and then subjected to measurement of agglutinativity by means of agglutination meter in the same platelet concentration. In addition, collagen was used as an agglutinant. As a control, a group to which no EPA was administered was also subjected to measurement of agglutinativity. The relative values of agglutinativity of the respective groups are shown in Table 2 (the value of the control group: 100).

TABLE 2

| Group | Control | EPA-EE | GL |
|---|---|---|---|
| Agglutinativity | 100 ± 8 | 65 ± 5 | 50 ± 5 |

As seen in this Table, it was confirmed that GL significantly more inhibits platelet agglutinativity than EPA-EE.

EXAMPLE 3

In order to investigate the difference between the absorptivity of EPA-EE and that of GL within the small intestine of rats, EPA-EE and GL each were orally administered only once (0.5 g/rat as EPA) under the same conditions as in Example 2. After 4 hours, the rats were killed, and substances remaining in the canal cavity of small intestine were collected and freeze-dried, followed by extracting the whole lipids therefrom and measuring the EPA content therein. The results are shown in Table 3. In addition, the blank was employed as control.

TABLE 3

| Group | Control | EPA-EE | GL |
|---|---|---|---|
| EPA residual quantity (g) | 0.005 | 0.154 | 0.052 |

As is apparent from Table 3, the absorptivity in the intestinal canal, of GL orally administered in considerably better than that of EPA-EE.

As to the glycolipid obtained according to the present invention, the EPA content in the fatty acids constituting the glycolipid is as high as 70% or more. According to the present invention, it is possible to obtain such a glycolipid by a simple operation of fractionating the whole lipids of marine Chlorella by means of a combination of solvent-fractionation and column chromatography.

Further, this glycolipid is characterized, as described in Examples, in that it has physiological effects of EPA such as platelet agglutination-inhibiting effect, etc., and yet has a higher absorption rate in the intestinal canal than EPA triglyceride or ethyl ester.

What we claim is:

1. A process for producing a glycolipid having a high eicosapentaenoic acid content, which comprises fractionating the whole lipids of marine Chlorella by extracting the whole lipids of marine Chlorella with a mixed solvent of a polar solvent with a non-polar solvent, thereafter removing the solvents from the extracted fluid, and then washing the residue with a non-polar solvent, and then subjecting the insoluble substance to column chromatography.

2. A process for producing a glycolipid having a high eicosapentaenoic acid content according to claim 1, wherein the fractionating is carried out by extracting the whole lipids of marine Chlorella with a mixed solvent of chloroform with methanol, thereafter removing the solvents from the extracted fluid, then washing the residue with diethyl ether, and then subjecting the insoluble substance to column chromatography.

3. A process for producing a glycolipid having a high eicosapentaenoic acid content according to claim 1, wherein silica gel is used for said column chromatography.

4. A process for producing a glycolipid having a high eicosapentaenic acid content according to claim 1, wherein said marine Chlorella is Chlorella minutissima.

5. A process for producing a glycolipid having a high eicosapentaenoic acid content according to claim 1, wherein the eicosapentaenoic acid content in the fatty acids constituting the glycolipid is 70% or more.

* * * * *